(12) United States Patent
Handlin, Jr. et al.

(10) Patent No.: US 8,188,192 B2
(45) Date of Patent: May 29, 2012

(54) SOFT ELASTOMERIC FILMS

(75) Inventors: Dale Lee Handlin, Jr., Shelby, NC (US); Phillip Doerpinghaus, Noble, OK (US); Sandra Horton, legal representative, Noble, OK (US); Keith Eiden, Houston, TX (US); Margaret Clawson, Ivanhoe, NC (US)

(73) Assignee: Kraton Polymers U.S. LLC, Houston, TX (US)

( * ) Notice: Subject to any disclaimer, the term of this patent is extended or adjusted under 35 U.S.C. 154(b) by 475 days.

(21) Appl. No.: 12/339,356

(22) Filed: Dec. 19, 2008

(65) Prior Publication Data

US 2009/0163361 A1 Jun. 25, 2009

Related U.S. Application Data

(60) Provisional application No. 61/015,913, filed on Dec. 21, 2007.

(51) Int. Cl.
*C08F 257/02* (2006.01)
(52) U.S. Cl. ............... 525/314; 525/332.9; 525/241; 525/901; 525/342; 526/337; 526/347; 526/938
(58) Field of Classification Search ............ 525/314, 525/332.9, 241, 901, 342; 526/337, 347, 526/938
See application file for complete search history.

(56) References Cited

U.S. PATENT DOCUMENTS

| | | |
|---|---|---|
| 3,494,942 A | 2/1970 | Miki et al. |
| RE27,145 E | 6/1971 | Jones |
| 3,634,594 A | 1/1972 | Hiyama |
| 3,670,054 A | 6/1972 | De La Mare |
| 3,700,633 A | 10/1972 | Wald et al. |
| 5,790,983 A | 8/1998 | Rosch et al. |
| 5,953,754 A | 9/1999 | Rosch et al. |
| 6,245,401 B1 | 6/2001 | Ying et al. |
| 6,497,694 B1 | 12/2002 | Rosch et al. |
| 6,846,535 B2 | 1/2005 | DeGroot et al. |
| 6,984,696 B2 | 1/2006 | Curry et al. |

(Continued)

FOREIGN PATENT DOCUMENTS

WO 0228965 A1 4/2002

OTHER PUBLICATIONS

Nairn "Polymer Structure and Characterization" 2007.*

(Continued)

*Primary Examiner* — Vasu Jagannathan
*Assistant Examiner* — Mark Kaucher
(74) *Attorney, Agent, or Firm* — Clements Bernard PLLC; Michael A. Masse (57) ABSTRACT

Elastomeric films which are both soft and thermally, UV and oxidatively stable are provided. The films are composed of coupled, selectively hydrogenated block copolymers having a relatively high molecular weight and high vinyl content. In addition to the block copolymer other components may be present in formulated films such as other block copolymers, hydrocarbon resins, polyolefins, metallocene polyolefins, homopolystyrene or mineral oils. The softness of the films is determined by the stress at 100% tensile elongation where the films with suitable softness have a 100% stress of about 100 psi or less. While soft, the films also are strong with tensile strengths of 1000 psi or more and suitable hysteresis properties. The elastomeric films are useful as integral components of personal hygiene articles such as gloves, diapers, incontinence products, disposable swimwear and disposable undergarments.

12 Claims, 2 Drawing Sheets

U.S. PATENT DOCUMENTS

| | | |
|---|---|---|
| 7,001,956 B2 | 2/2006 | Handlin, Jr. et al. |
| 7,009,000 B2 | 3/2006 | Bening et al. |
| 7,267,855 B2 | 9/2007 | Handlin, Jr. et al. |
| 7,582,702 B2 | 9/2009 | Wright et al. |
| 2005/0137348 A1* | 6/2005 | Bening et al. .................. 525/314 |
| 2005/0197464 A1 | 9/2005 | Handlin, Jr. et al. |
| 2005/0197465 A1 | 9/2005 | Handlin |
| 2005/0222356 A1 | 10/2005 | Joly et al. |
| 2006/0030665 A1 | 2/2006 | Joly et al. |
| 2007/0020473 A1 | 1/2007 | Umana et al. |
| 2007/0026251 A1 | 2/2007 | Umana et al. |
| 2007/0225429 A1* | 9/2007 | Wright et al. .................. 524/505 |

OTHER PUBLICATIONS

Kraton Polymers US LLC, Kraton Announces Styrenic Block Copolymers (SBC) as Alternatives to Polyvinyl Chloride (PVC) in Medical and Packaging Applications, Press Release, Jan. 11, 2006.

* cited by examiner

SOFT ELASTOMERIC FILMS

CROSS-REFERENCE TO RELATED APPLICATION

The present application claims priority from commonly assigned U.S. provisional patent application Ser. No. 61/015,913, filed Dec. 21, 2007, entitled Soft Elastomeric Films.

FIELD OF THE INVENTION

The invention relates to personal hygiene articles comprising soft elastomeric films of selectively hydrogenated block copolymers. The invention further relates soft elastomeric films comprising at least one selectively hydrogenated block copolymer.

BACKGROUND OF THE INVENTION

Disposable personal hygiene article such as gloves, diapers and incontinence products are in widespread use. Soft, elastic films are particularly useful for personal hygiene articles and their integral components. These articles and their integral components have specific physical requirements. Ideally, these films would meet a variety of properties in addition to softness. For instance, while soft, these films would also need to have sufficient strength and an ability to withstand significant elongation. Since the articles are generally used in at least a slightly stretched condition, the films also need to retain their strength and dimension over time and at body temperature and to apply an appropriate retractive force for their particular application. Further, the films need to be stable in their environments of use and of storage, both before and after construction of the personal hygiene article.

Soft elastomeric films consisting of isoprene rubber or styrene-isoprene-styrene block copolymers are well known. One reason for their application is the inherent softness and strength of polyisoprene. Polyisoprene is, however, unsaturated and susceptible to oxidative, thermal and UV degradation. Elastomeric films for commercial application are typically melt processed at high temperatures. Unsaturated films such as made from SIS are susceptible to thermal degradation during processing. This limits the temperatures and the amount of shear that unsaturated block copolymers can experience during processing. Further, because elastomeric films used for commercial applications are stored for some time before final product manufacture and product use, long term oxidative and UV stability is important. Also, the final fabricated article will be exposed to conditions that can lead to UV, oxidative or thermal degradation. Elastomeric films fabricated from unsaturated block copolymers, while soft, present limitations in this regard. It would be advantageous to have a saturated, or hydrogenated, block copolymer which could be melt processed into soft elastomeric films. However, without formulation with other softening components, saturated block copolymers such as SEBS generally lack the combined softness and strength required for these applications.

The present invention provides an elastomeric film made from selectively hydrogenated block copolymers which has the softness of conventional SIS-based films but the stability inherent in saturated conjugated diene rubbers. We have discovered that with the proper combination of block copolymer molecular weight, monoalkenyl arene content and rubber vinyl content such soft elastomeric films can be produced and because of their selectively hydrogenated nature will be stable to thermal, oxidative and UV environments.

SUMMARY OF THE INVENTION

In one embodiment the invention is a personal hygiene article comprising a soft elastomeric film consisting of a coupled, selectively hydrogenated block copolymer. The block copolymer has the general formula (A-B)nX where X is the residue of a coupling agent and n is from 2 to 6, the monoalkenyl arene A block has a molecular weight from 6000 to 7000, the vinyl content of the conjugated diene B block prior to hydrogenation is from 60 to 85%, the total molecular weight is from 180,000 to 400,000 and the monoalkenyl arene content is from 9 to 16% wt. The block copolymer is highly coupled such that the amount of uncoupled A-B arms is less than 10%.

In another embodiment the invention is a soft elastomeric film comprising one coupled, selectively hydrogenated block copolymer of relatively low molecular weight and a second coupled, selectively hydrogenated block copolymer of relatively high molecular weight. The relatively high molecular weight block copolymer has monoalkenyl arene A blocks with molecular weights from 6000 to 7000, a B block vinyl content from 60 to 85%, a total molecular weight from 180,000 to 400,000, a monoalkenyl arene content from 9 to 16% wt and less than 10% uncoupled diblock. The relatively low molecular weight block copolymer has monoalkenyl arene A blocks with molecular weights from 5000 to 7000, a vinyl content of the B block from 60 to 85%, a total molecular weight of 100,000 to 160,000, a monoalkenyl arene content from 16 to 24% wt and less than 10% uncoupled diblock.

In another embodiment the invention is a soft elastomeric film comprising one coupled, selectively hydrogenated block copolymer having monoalkenyl arene A blocks with molecular weights from 6000 to 7000, a B block vinyl content from 60 to 85%, a total molecular weight from 180,000 to 400,000, a monoalkenyl arene content from 9 to 16% wt and less than 10% uncoupled diblock and an additional component such as a hydrocarbon resin, a polyolefin, a metallocene polyolefin, homopolystyrene or mineral oil.

In another embodiment the invention is a soft elastomeric film comprising one coupled, selectively hydrogenated block copolymer having monoalkenyl arene A blocks with molecular weights from 6000 to 7000, a B block vinyl content from 60 to 85%, a total molecular weight from 180,000 to 400,000, a monoalkenyl arene content from 9 to 16% wt and less than 10% uncoupled diblock and a controlled distribution block copolymer.

DETAILED DESCRIPTION OF THE INVENTION

Figure 1:
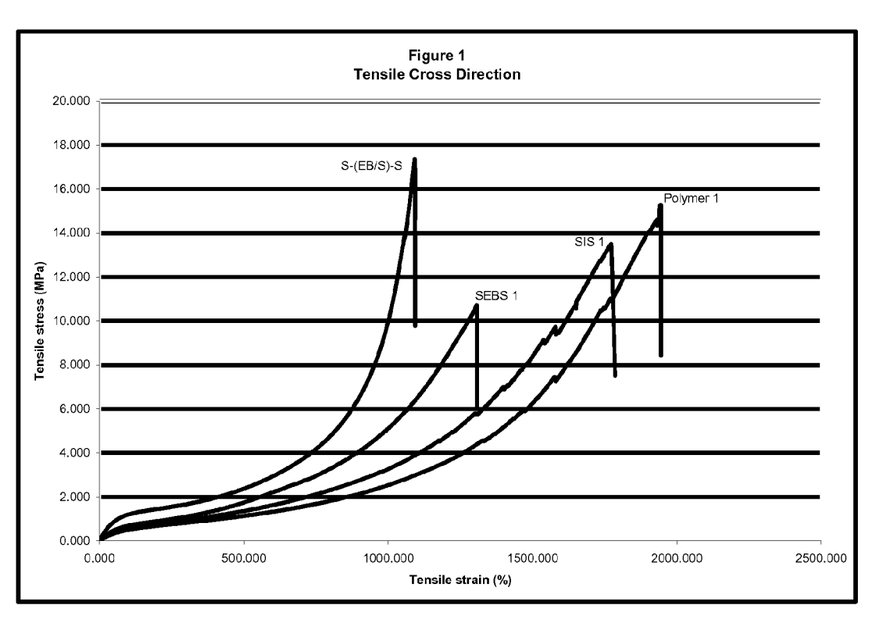
FIG. 1 shows the tensile strain response of Polymer 1, SEBS 1, SIS 1 and S-(EB/S)-S of extruded films in the cross direction.
Figure 2:
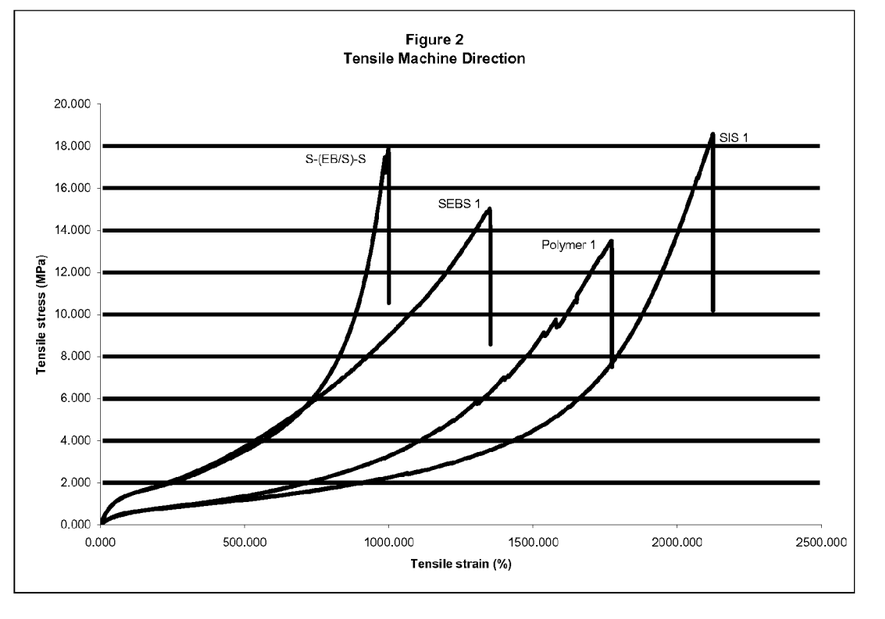
FIG. 2 shows the tensile strain response of Polymer 1, SEBS 1, SIS 1 and S-(EB/S)-S of extruded films in the machine direction.

The soft elastomeric films of the present invention are comprised of coupled, selectively hydrogenated block copolymers. The block copolymers have a general formula (A-B)nX where X is the residue of a coupling agent and n represents the average number of arms coupled. The block copolymers are synthesized using common anionic polymerization techniques.

The A block represents a polymerized monoalkenyl arene hydrocarbon block. The monoalkenyl arene can be selected from styrene, alpha-methylstyrene, para-methylstyrene, vinyl toluene, vinylnaphthalene, and para-butyl styrene or mixtures thereof. Of these, styrene is most preferred.

The B block represents a polymerized conjugated diene hydrocarbon block. The conjugated dienes can be selected from 1,3-butadiene and substituted butadienes. Of these, 1,3-butadiene is most preferred. As used herein, and in the claims, "butadiene" refers specifically to "1,3-butadiene". The vinyl content of the B block before hydrogenation is from 60 to 85% mol. More preferred are vinyl contents ranging from 65 to 85% mol and most preferred are vinyl contents ranging from 70 to 85% mol. The term vinyl means, for instance, 1,3-butadiene unit which are polymerized via 1,2-addition of the monomer to the living chain. In case of 1,3-butadiene the result is a mono-substituted olefin group pendant to the polymer backbone, a vinyl group. In the case of anionic polymerization of isoprene, as another example, the vinyl group results from a 3,4-addition of the polymerizing monomer. This affords a geminal dialkyl C=C group pendant to the polymer backbone. Vinyl configuration can be achieved by the use of a control agent during polymerization of the diene and by polymerization temperature. Any microstructure control agent known to those of ordinary skill in the art capable of preparing high vinyl conjugated dienes can be used to prepare the block copolymers of the present invention. Most preferred are microstructure control agents which are compatible with hydrogenation catalysts.

In one embodiment the coupled, selectively hydrogenated block copolymer has a relatively high molecular weight. The total molecular weight of the block copolymer is from 180,000 to 400,000. At molecular weights lower than 180,000 the polymer becomes too weak for the present application as a load bearing elastic film. At molecular weights higher than 400,000 the viscosity prohibits easy melt processing of the block copolymer. More preferred is the range from 200,000 to 300,000 and most preferred is the range from 210,000 to 270,000. The molecular weight of the monoalkenyl arene block is from 6000 to 7000. More preferred is the range from 6100 to 6800 and most preferred is the range from 6200 to 6700. The monoalkenyl arene content of the block copolymer is from 8 to 15% wt of the total block copolymer mass. At monoalkenyl arene contents less than 8% wt the elastic films have poor strength and at contents higher than 15% wt the films have reduced softness. More preferred is the range from 9 to 14% wt and most preferred is the range from 10 to 14% wt.

In another embodiment the relatively high molecular weight block copolymer is combined with a second coupled, selectively hydrogenated block copolymer having a relatively low molecular weight to form a soft elastic film. The relatively low molecular weight block copolymer has a total molecular weight from 100,000 to 160,000. More preferred is the range from 110,000 to 150,000 and most preferred is the range from 120,000 to 150,000. The molecular weight of the monoalkenyl arene block is from 5000 to 7000. More preferred is the range of 5500 to 7000 and most preferred is the range from 6000 to 7000. The monoalkenyl arene content of the block copolymer is from 16 to 24% wt of the total block copolymer mass. More preferred is the range from 17 to 23% wt and most preferred is the range from 18 to 22% wt. In this embodiment the relatively high molecular weight block copolymer is present in an amount from 15 to 40 parts by weight of the total composition. The second block copolymer is present in an amount from 60 to 85 parts by weight. More preferred is an amount from 20 to 30 parts by weight of the relatively high molecular weight block copolymer and 70 to 80 parts by weight of the second block copolymer.

In a further embodiment the relatively high molecular weight block copolymer is combined with a second selectively hydrogenated controlled distribution block copolymer. Controlled distribution block copolymers useful for this invention are described in U.S. Pat. No. 7,169,848. The second block copolymer has a general configuration A'-B', A'-B'-A', (A'-B')n, (A'-B'-A')nX, (A'-B')nX or mixtures thereof wherein prior to hydrogenation each A' block is a monoalkenyl arene polymer block and each B' block is a controlled distribution copolymer block of at least one conjugated diene and at least one monoalkenyl arene. Subsequent to hydrogenation about 0-10% of the arene double bonds have been reduced, and at least about 90% of the conjugated diene double bonds have been reduced. Each A' block has a molecular weight between about 3,000 and about 60,000 and each B' block has a molecular weight between about 30,000 and about 300,000. In the case of this controlled distribution block copolymer, the molecular weights are expressed as true peak molecular weights. They have been corrected for composition from the apparent GPC molecular weights. Each B' block comprises terminal regions adjacent to the A' block that are rich in conjugated diene units and one or more regions not adjacent to the A' blocks that are rich in mono alkenyl arene units. The total amount of monoalkenyl arene in the hydrogenated block copolymer is about 20 percent weight to about 80 percent weight. The weight percent of monoalkenyl arene in each B' block is between about 10 percent and about 75 percent. The monoalkenyl arene blockiness in the B' block is less than 40%. In the preferred embodiment the controlled distribution block copolymer has the structure (A'-B')nX, where the coupling agent is methyl-trimethoxy silane and the polymer has been coupled such that 7% or less uncoupled arms remain and the fraction with n=2 makes up 80% or greater, most preferably 90% or greater. Further, the A' block is polymerized styrene and has a molecular weight from 8,000 to 12,000, the overall molecular weight is from 120,000 to 160,000, and the overall styrene content is from 38 to 46%. The B' block has from 15 to 40% styrene and the styrene blockiness index of the B' block is less than 10%.

Except as specifically noted for the controlled distribution block copolymers, the term "molecular weights" in this specification refers to the apparent molecular weight in g/mol of the polymer or block of the copolymer. The molecular weights referred to in this specification and these claims can be measured with gel permeation chromatography (GPC) using polystyrene calibration standards, such as is done according to ASTM 3536. GPC is a well-known method wherein polymers are separated according to molecular size, the largest molecule eluting first. The chromatograph is calibrated using commercially available polystyrene molecular weight standards. The molecular weight of polymers measured using GPC so calibrated are styrene equivalent, or apparent, molecular weights. The apparent molecular weight may be converted to true molecular weight when the styrene content of the polymer and the vinyl content of the diene segments are known. The detector used is preferably a combination ultraviolet and refractive index detector. Unless otherwise noted, the molecular weights expressed herein are measured at the peak of the GPC trace and are commonly referred to as "peak molecular weights".

In the general formula for the coupled polymer, (A-B)nX, X is the residue of a coupling agent and n represents the average number of living arms per coupled block copolymer. In the present invention n is preferably from about 2 to about 15 and most preferably from 2 to 6. When n is 2 the block copolymer has a linear configuration. When n is greater than 2 the block copolymer is referred to as radial, branched or star.

The coupling reaction may be conducted to link only a fraction of the living arms or may be conducted to yield highly coupled polymers. In general, the amount of living arm which is linked in the coupling reaction is reported by a "coupling efficiency" measurement. Importantly, the coupling is generally a statistical process and n is an average number of coupled arms as taught in U.S. Pat. Nos. 7,001,956 and 7,009,000.

In the present invention, the preferred coupling agent is an alkoxy silane of the general formula Rx-Si—(OR')y, where x is 0 or 1, x+y=3 or 4, R and R' are the same or different, R is selected from aryl, linear alkyl and branched alkyl hydrocarbon radicals, and R' is selected from linear and branched alkyl hydrocarbon radicals. The aryl radicals preferably have from 6 to 12 carbon atoms. The alkyl radicals preferably have 1 to 12 carbon atoms, more preferably from 1 to 4 carbon atoms. Under melt conditions these alkoxy silane coupling agents can couple further to yield functionalities greater than 4. Preferred tetra alkoxy silanes are tetramethoxy silane ("TMOS"), tetraethoxy silane ("TEOS"), tetrabutoxy silane ("TBOS"), and tetrakis-(2-ethylhexyloxy)-silane ("TEHOS"). Of these the most preferred is tetramethoxy silane.

The hydrogenated block copolymers of the present invention are selectively hydrogenated using any of the several hydrogenation processes know in the art. For example the hydrogenation may be accomplished using methods such as those taught, for example, in U.S. Pat. Nos. 3,494,942; 3,634,594; 3,670,054; 3,700,633; and Re. 27,145, the disclosures of which are hereby incorporated by reference. Any hydrogenation method that is selective for the double bonds in the conjugated polydiene blocks, leaving the aromatic unsaturation in the polystyrene blocks substantially intact, can be used to prepare the hydrogenated block copolymers of the present invention.

The methods known in the prior art and useful for preparing the hydrogenated block copolymers of the present invention involve the use of a suitable catalyst, particularly a catalyst or catalyst precursor comprising an iron group metal atom, particularly nickel or cobalt, and a suitable reducing agent such as an aluminum alkyl. Also useful are titanium based catalyst systems. In general, the hydrogenation can be accomplished in a suitable solvent at a temperature within the range from about 20° C. to about 100° C., and at a hydrogen partial pressure within the range from about 100 psig (689 kPa) to about 5,000 psig (34,473 kPa). Catalyst concentrations within the range from about 10 ppm to about 500 ppm by wt of iron group metal based on total solution are generally used and contacting at hydrogenation conditions is generally continued for a period of time with the range from about 60 to about 240 minutes. After the hydrogenation is completed, the hydrogenation catalyst and catalyst residue will, generally, be separated from the polymer.

In the present invention, the hydrogenated block copolymers have a hydrogenation degree greater than 80% mol. This means that more than from 80% mol of the conjugated diene double bonds in the B block have been hydrogenated from an alkene to an alkane. Preferably, greater than about 90% mol of the conjugated dienes are hydrogenated. Most preferably, greater than about 95% mol of the conjugated dienes are hydrogenated.

The hydrogenation is selective such that while high degrees of hydrogenation of the conjugated diene are achieved only minimal hydrogenation of the monoalkenyl arene occurs. In the practice of this invention 0-10% mol of the monoalkenyl arene units are hydrogenated. Preferably, less than 5% mol of the monoalkenyl arene units are hydrogenated. More preferably, less than 1% mol of the monoalkenyl arene units are hydrogenated.

In one embodiment of the invention the coupled, selectively hydrogenated block copolymer is combined with another polymer component. The polymer component may be a hydrocarbon resin, a polyolefin, a metallocene polyolefin, homopolystyrene or a mineral oil.

Hydrocarbon resins compatible with the hydrogenated, conjugated diene block are particularly useful in the present invention. The hydrocarbon resins compatible may be selected from the group consisting of compatible C5 hydrocarbon resins, hydrogenated C5 hydrocarbon resins, C5/C9 resins, fully hydrogenated or partially hydrogenated C9 hydrocarbon resins and mixtures thereof. Examples of commercial hydrocarbon resins suitable for the invention are OPPERA® and ESCOREZ® from ExxonMobil Chemical, and REGALITE® and REGALREZ® from Eastman Chemical. The amount of hydrocarbon resin in the elastomer film is from 5 to 35% wt based on the elastomer film mass. More preferred is 5 to 15% wt of hydrocarbon resin.

Examples of metallocene polyolefins include ethylene/alpha-olefin copolymers, propylene/alpha-olefin copolymers and ethylene/propylene/alpha-olefin terpolymers such as AFFINITY®, ENGAGE® and VERSIFY® polymers from Dow Chemical and EXACT® and VISTAMAXX® polymers from Exxon Mobil.

Examples of homopolystyrene resins include resins having melt flow rates less than 10 g/10 min at 200° C./5 kg such as PS2500 from Nova Chemical and resins having melt flow rates of greater than 30 g/10 min at 200 C/5 kg such as PS 3900 from Nova Chemical. The melt flow is preferably from 3 to 38 and more preferably from 4 to 18. The total monoalkenyl arene content of the composition including both the block copolymer and the homopolystyrene is less than 20% wt. The more preferred total monoalkenyl arene content is 15% wt or less.

Examples of mineral oils include oils which are compatible with the elastomeric mid-block segment of the elastomeric block copolymer and which do not tend to migrate into the aromatic endblock portions to any significant degree. Specific examples are paraffinic oils such as Drakeol 34 from Penreco. The preferred amount of mineral oil is 10 parts by weight for every hundred parts of block copolymer or less. Because high levels of mineral oil can lead to tacky films or an oil surface film on the material, the amount of oil is to be minimized. The more preferred amount of oil is 5 parts by weight or less. In the most preferred embodiments the softness of the elastomeric film or personal hygiene article is achieved with no oil.

While the high vinyl block copolymers can be blended with the polymers and resins taught herein to form the soft elastic films of the present invention, unsatisfactory results are achieved when they are blended with a significant amount of homo-polypropylenes or polypropylene copolymers made from conventional Ziegler-Natta catalysis. The films contain less than 10% of such homo-polyproylenes or propylene copolymers, preferably less than 5% and most preferably 0%.

The soft elastomeric films can be produced using conventional melt processing equipment. A specific example of suitable equipment for melt processing is a Killion 30:1 KL100 1 inch single screw extruder with a 6 inch film die. Larger size single screw extruders with larger dies may also be used. Importantly, the soft elastomeric films of the present invention are characterized by low rubber moduli and sufficiently high tensile strengths. For the purposes of the present invention, soft means having a stress at 100% tensile elongation less than about 100 psi and a stress at 300% tensile elongation less than about 150 psi. In order for these soft films to have practical utility they must also have tensile strengths of at least about 1000 psi. These tensile properties are importantly measured in the machine direction of melt cast films. Under common operating conditions, melt extrusion operations can lead to the development of structure within extruded block copolymer films. Such structure can in turn result in high stiffness and/or yield stress which decreases the softness in the machine direction. In general, soft elastomeric films meeting these conditions also have tensile elongations of at least 500%.

The reduced tensile stress, or increased softness, leads to enhanced drape of the films. This is particularly important for the applications of the invention where the films are applied in personal hygiene articles such as gloves.

Hysteresis properties are also important because the elastomeric films of the present invention will be subject to cyclic stresses during use. The hysteresis properties most characteristic of the elastic films are the recovered energy, the percent set after a cyclic tensile stress and the peak stress experienced during the cycle. The soft elastomeric films of the present invention have recovered energies ranging from 40 to 70%, percent set ranging from 30 to 70% and peak stresses ranging from 116 psi to 218 psi in hysteresis cycles to 300% elongation. In cycles to 100% elongation the films have recovered energies ranging from 55 to 90%, percent set ranging from 7 to 18% and peak stresses ranging from 70 to 160 psi.

The films of the present invention are useful in personal hygiene articles such as gloves, diapers, incontinence products, disposable undergarments, disposable swimwear for children and the like. The personal hygiene articles may be composed essentially of the soft elastomeric film alone as in the case of gloves. In the more complex articles such as diapers, incontinence products, undergarments and swimwear, the soft elastomeric film may make up one or more integral components to the article. Such integral components may be stretch panels, elastic closures, waistbands and the like.

EXAMPLES

Materials

Polymer 1 is a coupled, selectively hydrogenated block copolymer. Polymer 1 is a polymer of the invention. The structure of Polymer 1 is (S-EB)nX where S is a polystyrene block having a molecular weight of about 6400, EB is a hydrogenated polybutadiene block having a vinyl content of 77% before hydrogentation, the total apparent molecular weight is about 235,000 and the total styrene content is 12.5%.

SEBS 1 is a coupled, selectively hydrogenated block copolymer. When used alone to make elastic films SEBS 1 is a comparative polymer. When used in combination with Polymer 1, SEBS 1 is a polymer of the invention. The structure of SEBS 1 is (S-EB)nX where S is a polystyrene block having a molecular weight of about 6200, EB is a hydrogenated polybutadiene block having a vinyl content of 77% before hydrogenation, the total apparent molecular weight is about 143,000 and the total polystyrene content is 20%.

SEBS 2 is a comparative polymer and is a coupled, selectively hydrogenated block copolymer. The structure of SEBS 2 is (S-EB)2 where S is a polystyrene block having a molecular weight of about 5300, EB is a hydrogenated polybutadiene block having a vinyl content of about 40% before hydrogenation, the total apparent molecular weight is about 145,000 and the total polystyrene content is 13%.

SIS 1 is a comparative polymer and is an unsaturated block copolymer. The structure of SIS 1 is S-I-S where S is a polystyrene block having a molecular weight of about 11,100, I is a polyisoprene block, the total apparent molecular weight is about 178,000 and the total polystyrene content is 19%.

SIS 2 is a comparative polymer and is an unsaturated block copolymer. The structure of SIS 2 is S-I-S where S is a polystyrene block having a molecular weight of about 13,000, I is a polyisoprene block, the total apparent molecular weight is about 126,000 and the total polystyrene content is 29%.

S-(EB/S)-S is a comparative polymer and is a selectively hydrogenated block copolymer. S is a styrene block having a molecular weight of about 10,600, EB/S is a selectively hydrogenated controlled distribution copolymer block of styrene and butadiene where this block has 25% styrene and a styrene blockiness index of about 5%, the total apparent molecular weight is about 40,000 and the total styrene content is 42%.

Oppera PR100 is a hydrogenated hydrocarbon resin having a softening point of about 138° C. from ExxonMobil.

Piccotac 9095 is an aromatic modified C5 resin having a softening point of 94° C. and available from Eastman Chemical.

PS2500 and PS3900 are homopolystyrenes having melt flow indices of 7 g/10 min and 30 g/10 min, respectively, and are commercially available from Nova Chemical.

Vistamaxx 1100, 1120 and 2125 are metallocene catalyzed polyolefin copolymers commercially available from ExxonMobil. Vistamaxx 1100 has a melt flow rate of 3.0 g/10 min at 230° C./2.16 kg and a density of 0.860 g/cm3. Vistamaxx 1120 has a melt flow rate of 21 at 230° C./2.16 kg and a density of 0.861 g/cm3. Vistamaxx 2125 has a melt flow rat of 80 g/10 min at 230° C./2.16 kg and a density of 0.865 g/cm3.

Elvax 250 is an ethylene-vinyl acetate copolymer resin having 28% wt vinyl acetate and a melt flow rate of 25 g/10 min at 190° C./2.16 kg and is commercially available from DuPont.

Irganox 1010 is a phenolic antioxidant and Irgafos 168 is diarylalkyl phosphate stabilizer, both available from Ciba.

Processing Procedures

Compound blends were made by premixing all compound components then extruding the preblend on a 25 millimeter Berstorff twin screw extruder at a melt temperature of approximately 205° C. for compounds containing unhydrogenated polymer and approximately 220-227° C. for compounds containing hydrogenated polymer. The finished compounds were then cast into approximately 125 micron thick films on a Killion 30:1 KL100 1 inch single screw extruder with a 6 inch film die. The die temperature was approximately 205° C. for compounds containing unhydrogenated polymer and 232-249° C. for compounds containing hydrogenated polymer.

Example 1

Elastomeric films were made by compression molding or melt casting. Films made from Polymer 1 were compared to conventional films made from SEBS and SIS.

Table 101 lists the tensile results for Polymer 1 and SEBS 1 elastomeric films. The tensile properties were measured according to ASTM D412. The tensile test specimens were cut from a melt pressed film using a D die. The tensile tests were conducted using a 500 mm/min crosshead speed and at a temperature of 23° C. These results show that soft elastomeric films having a 100% stress of about 100 psi or less and a tensile strength greater than 1000 psi can be made with neat Polymer 1. The film made with SEBS 1 had a relatively high 100% stress at 160 psi and would be unsuitable as a neat polymer for the soft elastic films of the invention.

Table 102 lists the tensile results for Polymer 1, SEBS 2, SIS 1 and SIS 2. The tensile test specimens were cut from melt extruded films in the machine and in the cross, or transverse, directions using a C die. These results show that Polymer 1 is able to make elastomeric films as soft as those made from SIS 1 which, while unsaturated, is commonly used to make soft elastomeric films and is substantially better than SIS 2, a relatively high styrene content SIS. While SEBS 2 has a comparable styrene content to Polymer 1 its 100% stress in the machine direction is 142 psi, greater than the 82 psi 100% stress of Polymer 1 by a factor of 1.7.

Table 103 lists the 100% hysteresis results for elastomeric films made from Polymer 1, SEBS 2, SIS 1 and SIS 2. The tests were performed on samples cut in the machine direction and on those cut in the cross, or transverse, direction. These results show that Polymer 1 is able to make elastomeric films as soft as those made from SIS 1 which, while unsaturated, is commonly used to make soft elastomeric films and is substantially better than SIS 2, a relatively high styrene content SIS. While SEBS 2 has a comparable styrene content to Polymer 1 its 100% stress in the machine direction under these conditions is 225 psi, greater than the 91 psi 100% stress of Polymer 1 by a factor of 2.5. In addition, the films of Polymer 1 have the lowest permanent set and the highest elastic ratios of all the films tested.

Example 2

Elastomeric films made from blends of block copolymer and hydrocarbon resins were prepared by melt casting.

Table 201 lists the hysteresis results for blends of Polymer 1 and a hydrocarbon resin, Oppera PR110, at various resin levels. Oppera PR110 is a hydrogenated hydrocarbon resin. Films were also made from Piccotac 9095, a aromatic modified C5 resin. The tests were performed on samples cut from melt pressed films using a microtensile die.

The results show that elastomeric films containing block copolymers of the present invention and hydrocarbon resins up to a level of 20% have 100% stress characteristic of soft films. When the resin was Oppera the films maintained a 100% modulus less than 100 psi for resin levels ranging from 5 to 20% wt of the total mass of block copolymer plus resin (Examples A-D). Further, the tensile set of these films was less than about 10% after elongation to 200%. When the resin was Piccotac 9095 (Examples E-F), low 100% moduli indicating sufficient softness were observed. However, these films had significantly higher tensile sets after 200% elongation. At the 10% wt and 20% wt resin levels the tensile sets were 14.4 and 12.2% respectively after one elongation cycle and 15.4 and 13.2% after the second cycle. Elastomeric films made with hydrogenated hydrocarbon resins were shown to have a significantly better combination of softness and dimensional stability than those made with the aromatic modified resins.

Example 3

Elastomeric films were melt cast from blends of Polymer 1 and various metallocene polyolefins at various levels. Table 301 lists the hysteresis results for blends of Polymer 1 and a metallocene polyolefins Vistamaxx 2125 and Vistamaxx 1120. The tensile properties were measured in the cross, or transverse, direction.

The elastomeric films with Vistamaxx 1120 at the 25 and 50% level were suitable for the soft films of the present application having 100% stress of 91.6 and 101.5% respectively. Vistamaxx 1120 provided suitable performance but blends with Vistamaxx 1100 or Vistamaxx 2125 did not provide suitable performance.

Example 4

Elastomeric films were melt cast from blends of Polymer 1 and homopolystyrene at various levels. Two grades of homopolystyrene were used: PS 2500 having a melt flow rate of 7.0 g/10 min at 200° C./5 kg and a flexural modulus of 3450 MPa and PS 3900 having a melt flow rate of 38 g/10 min at 200° C./5 kg and a flexural modulus of 3000 MPa. The PS 2500 is a relatively viscous and stiff homopolystyrene. The blends were made to match total polystyrene composition targets. The total polystyrene content is calculated as the weight percent of polystyrene basis the total amount of block copolymer and homopolystyrene. The tensile test specimens were cut from melt extruded films in the machine and in the cross, or transverse, directions using a C-type die.

Table 401 shows the results. The results show that elastomeric films having suitable softness can be made with Polymer 1 and PS 2500 up to 15% total polystyrene content (PSC) and also with Polymer 1 and PS 3900 up to 15% total polystyrene content (PSC). At this homopolystyrene level the elastomeric films had a 100% stress of approximately 80-90 psi when tested in the machine direction and approximately 75-85 psi when tested in the cross direction.

Example 5

Table 501 lists the tensile properties of elastomeric films made with various levels of S-(EB/S)-S. The tensile test specimens were cut from melt extruded films in the machine and in the cross, or transverse, directions using a C-type die.

Example 6

Elastomeric films were melt cast from blends of Polymer 1 and Elvax 250. The elastomeric films were composed of a blend of Polymer 1/Elvax 250 at ratios of 90/10 and 80/20 parts by weight. The tensile test specimens were cut from melt extruded films in the machine and in the cross, or transverse, directions using a C-type die.

Table 601 lists the tensile properties of the elastomeric films.

Example 7

Elastomeric films were melt cast from blends of Polymer 1 and SIS 2. The elastomeric films were composed of a blend of Polymer 1 and SIS 2 at a ratio of 70/30 parts by weight. The tensile samples were cut from a melt extruded film using a C-type die. The tests were performed on samples cut in the machine direction and on those cut in the cross, or transverse, direction.

Table 701 lists the tensile properties of the elastomeric films.

Table 702 lists the hysteresis properties of an elastomeric film composed of a blend of Polymer 1 and SIS 2 at a 70:30 weight ratio. Results for SEBS 1 and 2 are also listed. The samples were cut from a melt extruded film using a strip die (3 inches×0.5 inches). The hysteresis test protocol consisted of an activation elongation of 500%, a first hysteresis cycle to 200% and a second hysteresis cycle to 200%.

Example 8

Table 801 lists the tensile properties of elastomeric films composed of a blend of Polymer 1 and SEBS 1. The samples were cut from a melt extruded film using a C-type die in both the machine and cross, or transverse, direction.

TABLE 101

|  | Polymer | |
|---|---|---|
|  | Polymer 1 | SEBS 1 |
| Tensile strength (psi) | 1407 | 1566 |
| Elongation at break (%) | 780 | 680 |
| 100% modulus (psi) | 87 | 160 |
| 300% modulus (psi) | 160 | 319 |

TABLE 102

|  | 50% mod, psi | | 100% mod, psi | | 200% mod, psi | | 300% mod, psi | | Elongation, $l/l_o$ | | Strength, psi | |
|---|---|---|---|---|---|---|---|---|---|---|---|---|
|  | cross | machine | cross | machine | cross | machine | cross | machine | cross | machine | cross | machine |
| Polymer 1 | 48.6 | 54.7 | 73.1 | 81.6 | 99.9 | 113 | 120 | 138 | 19.37 | 16.67 | 2139 | 1656 |
| SIS 1 | — | — | 68.0 | 74.1 | — | — | 118 | 135 | 15.4 | 15.52 | 2056 | 1818 |
| SIS 2 | — | — | 139 | 343 | — | — | 219 | 503 | 13.65 | 12.49 | 3695 | 3137 |
| SEBS 2 | — | — | 138 | 142 | — | — | 192 | 202 | 14.53 | 14.61 | 2445 | 2695 |

TABLE 103

| Polymer | basis wt (g/m²) | | 100% stress (psi) | | perm set (%) | | 70% stress cyc2 return (psi) | | 50% stress cyc2 return (psi) | | 30% stress cyc2 return (psi) | | Elastic ratio 50% unld/100% load (psi) | | Elastic ratio 30% unld/100% load (psi) | |
|---|---|---|---|---|---|---|---|---|---|---|---|---|---|---|---|---|
|  | cross | machine | cross | machine | cross | machine | cross | machine | cross | machine | cross | machine | cross | machine | cross | machine |
| Polymer 1 | 105.0 | 103.4 | 82 | 91 | 7.8 | 7.2 | 60 | 67 | 48 | 53 | 30 | 33 | 0.59 | 0.58 | 0.37 | 0.36 |
| SEBS 2 | 110 | 97 | 232 | 225 | 8.17 | 12.25 | 116 | 115 | 89.0 | 86.0 | 50.0 | 46.0 | 0.38 | 0.38 | 0.22 | 0.20 |
| SIS 1 | 117.9 | 114.7 | 70.9 | 91.6 | 12.6 | 10.4 | 47.9 | 63.7 | 36.2 | 48.5 | 21.7 | 29.7 | 0.51 | 0.53 | 0.31 | 0.32 |
| SIS 2 | 121.5 | 125.7 | 134 | 316 | 9.4 | 10.4 | 87 | 173 | 70 | 139 | 46 | 97 | 0.52 | 0.44 | 0.34 | 0.31 |

TABLE 201

|  | A | B | C | D | E | F |
|---|---|---|---|---|---|---|
| Formulation (parts by weight) | | | | | | |
| Polymer 1 | 209 | 198 | 187 | 176 | 100 | 100 |
| Oppera PR100 | 11 | 22 | 33 | 44 | | |
| Piccotac 9095 | | | | | 11 | 25 |
| Irganox 1010 | 0.66 | 0.66 | 0.66 | 0.66 | 0.15 | 0.15 |
| Iragafos 168 | | | | | 0.3 | 0.3 |
| Percent hydrocarbon resin | 5 | 10 | 15 | 20 | 10 | 20 |
| Melt Flow, 230° C./5 kg | 21 | 34 | 56 | 93 | | |
| Tensile Results | | | | | | |
| 25% Modulus, psi | 40 | 37 | 34 | 30 | 30 | 30 |
| 50% Modulus, psi | 66 | 60 | 55 | 50 | 50 | 50 |
| 100% Modulus, psi | 95 | 85 | 80 | 71 | 72 | 71 |
| 200% Modulus, psi | 134 | 121 | 112 | 100 | 104 | 101 |
| 300% Modulus, psi | 176 | 160 | 149 | 132 | 139 | 132 |
| 500% Modulus, psi | 296 | 272 | 259 | 225 | 241 | 219 |
| Ultimate Stress, psi | 1910 | 1824 | 2528 | 2437 | 850 | 1431 |
| Ultimate Strain, % | 1152 | 1212 | 1432 | 1440 | 946 | 1186 |
| Hysterisis Results | | | | | | |
| Cycle 1 50% Load, psi | 59.8 | 55.0 | 50.3 | 46.8 | 51.6 | 43.2 |
| Cycle I 200% Load, psi | 116 | 106 | 97.2 | 90.5 | 95.7 | 80.1 |
| Cycle 1 50% Unload, psi | 49.3 | 43.5 | 40.5 | 37.0 | 37.4 | 31.9 |
| Cycle 1 Tensile Set, % | 7.8 | 8.1 | 8.7 | 9.5 | 14.4 | 12.2 |
| Cycle 1 Recovered Energy, % | 91.3 | 90.6 | 90 | 89.3 | 86.6 | 87.0 |
| Cycle 2 50% Load, psi | 53.4 | 48.7 | 44.2 | 40.9 | 40.9 | 35.4 |
| Cycle 2 200% Load, psi | 114 | 105 | 95.9 | 88.6 | 94.4 | 78.9 |
| Cycle 2 50% Unload, psi | 48.2 | 43.5 | 39.3 | 35.7 | 36.1 | 30.9 |
| Cycle 2 Tensile Set, % | 8.6 | 9 | 9.7 | 10.6 | 15.4 | 13.2 |
| Cycle 2 Recovered Energy, % | 95.4 | 94.9 | 94.6 | 93.9 | 94.9 | 94.2 |

TABLE 301

|  | Recovery Energy % | % Set | Peak Stress, psi |
|---|---|---|---|
| 100% hysteresis |  |  |  |
| Polymer 1-Vistamaxx 1120 (75-25) | 70.78 | 17.18 | 91.6 |
| Polymer 1-Vistamaxx 1120 (50-50) | 64.41 | 17.72 | 101.5 |
| Polymer 1-Vistamaxx 1120 (25-75) | 57.78 | 16.69 | 151.2 |
| Polymer 1-Vistamaxx 1100 (50-50) | 69.79 | 12.42 | 147.5 |
| Polymer 1-Vistamaxx 2125 (50-50) | 58.98 | 17.28 | 144.4 |
| 300% hysteresis |  |  |  |
| Polymer 1-Vistamaxx 1120 (75-25) | 69.55 | 35.33 | 139.9 |
| Polymer 1-Vistamaxx 1120 (50-50) | 56.29 | 57.67 | 135.1 |
| Polymer 1-Vistamaxx 1120 (25-75) | 41.68 | 65.28 | 193.5 |
| Polymer 1-Vistamaxx 1100 (50-50) | 59.38 | 38.47 | 199.7 |
| Polymer 1-Vistamaxx 2125 (50-50) | 48.07 | 47.79 | 203.5 |

TABLE 401

|  | 50% mod, psi | | 100% mod, psi | | 200% mod, psi | | 300% mod, psi | | Elongation, l/l$_o$ | | Strength, psi | |
|---|---|---|---|---|---|---|---|---|---|---|---|---|
|  | cross | machine | cross | machine | cross | machine | cross | machine | cross | machine | cross | machine |
| Polymer 1/PS2500 |  |  |  |  |  |  |  |  |  |  |  |  |
| 15% total PSC | 47.3 | 59.5 | 70.9 | 88.8 | 96.3 | 125 | 116 | 158 | 16.66 | 13.21 | 1474 | 1095 |
| 20% total PSC | 54.0 | 132 | 77.4 | 179 | 101 | 246 | 122 | 318 | 17.92 | 14.2 | 1951 | 2139 |
| 30% total PSC | 94.1 | 475 | 129 | 575 | 178 | 731 | 235 | 879 | 16.27 | 12.14 | 2376 | 2824 |
| Polymer 1/PS3900 |  |  |  |  |  |  |  |  |  |  |  |  |
| 15% total PSC | 51.9 | 55.5 | 76.4 | 83.5 | 105 | 117 | 127.6 | 145.5 | 16.2 | 15.6 | 2193 | 2129 |

TABLE 501

|  | 50% mod, psi | | 100% mod, psi | | 200% mod, psi | | 300% mod, psi | | Elongation, l/l$_o$ | | Strength, psi | |
|---|---|---|---|---|---|---|---|---|---|---|---|---|
| Polymer 1/S-(EB/S)-S | cross | machine | cross | machine | cross | machine | cross | machine | cross | machine | cross | machine |
| 70/30 | 57.9 | 136 | 83.1 | 171 | 106 | 211 | 124 | 249 | 14.11 | 14.25 | 876 | 1645 |
| 50/50 | 89.6 | 151 | 125 | 194 | 154 | 242 | 177 | 287 | 15.9 | 12.64 | 2387 | 1442 |
| 30/70 | 92.7 | 162 | 127 | 205 | 153 | 256 | 174 | 305 | 15.33 | 10.64 | 2792 | 1331 |

TABLE 601

| Polymer | 50% mod, psi | | 100% mod, psi | | 200% mod, psi | | 300% mod, psi | | elongation, l/l$_o$ | | Strength, psi | |
|---|---|---|---|---|---|---|---|---|---|---|---|---|
| 1/Elvax 250 | cross | machine | cross | machine | cross | machine | cross | machine | cross | machine | cross | machine |
| 90/10 | 63.7 | 90.9 | 91.2 | 131 | 119 | 170 | 141 | 203 | 19.16 | 13.97 | 1690 | 1521 |
| 80/20 | 106 | 156 | 138 | 197 | 168 | 237 | 196 | 278 | 20.45 | 17.3 | 1935 | 2466 |

TABLE 701

|  | SEBS 1 | | Polymer 1/SIS 2 | |
|---|---|---|---|---|
| Property | cross | machine | cross | machine |
| 50% modulus, psi | 68 | 119 | 65 | 140 |
| 100% modulus, psi | 100 | 183 | 93 | 184 |
| 200% modulus, psi | 138 | 255 | 117 | 231 |
| 300% modulus, psi | 177 | 318 | 138 | 277 |
| Ultimate Stress, psi | 1929 | 1388 | 1987 | 1905 |
| Ultimate Strain, mm/mm | 15.56 | 11.26 | 18.96 | 14.73 |

TABLE 702

| Property | SEBS2 cross | SEBS2 Machine | SEBS1 cross | SEBS1 machine | Polymer1/SIS2 cross | Polymer1/SIS2 machine |
|---|---|---|---|---|---|---|
| 500% stress, psi | 476.05 | 494.01 | 681.35 | 1195.73 | 308.38 | 573.89 |
| Tensil set after 500%, % | 29.19 | 28.43 | 25.89 | 36.94 | 9 | 8.08 |
| 200% load prestrain, psi | 196.76 | 197.42 | 162.39 | 204.95 | 132.91 | 167.78 |
| 200% stress C1, psi (hold) | 190.52 | 191.32 | 156.83 | 196.64 | 129.57 | 163.99 |
| 50% unload stress C2, psi | 79.98 | 79.58 | 69.24 | 76.28 | 62.79 | 73.82 |
| 30% unload stess C2 psi | 51.41 | 50.91 | 49.31 | 55.73 | 45.86 | 54.16 |
| ratio 50% unld C2/200% C1 | 0.41 | 0.40 | 0.43 | 0.37 | 0.47 | 0.44 |
| ratio 30% unld C2/200% C1 | 0.26 | 0.26 | 0.30 | 0.27 | 0.35 | 0.32 |
| 500% stress, N | 5.29 | 5.494 | 7.58 | 13.297 | 2.743 | 5.106 |
| 200% stress C1, N (prestrain) | 2.19 | 2.2 | 1.81 | 2.28 | 1.18 | 1.493 |
| 50% unload stress C2, N | 0.89 | 0.89 | 0.77 | 0.85 | 0.559 | 0.657 |
| 30% unload stess C2 N | 0.57 | 0.57 | 0.548 | 0.62 | 0.408 | 0.482 |
| ratio 50% unld C2/200% C1 | 0.41 | 0.40 | 0.43 | 0.37 | 0.47 | 0.44 |
| ratio 30% unld C2/200% C1 | 0.26 | 0.26 | 0.30 | 0.27 | 0.35 | 0.32 |

TABLE 801

| | 50% mod, psi | | 100% mod, psi | | 200% mod, psi | | 300% mod, psi | | Elongation, $l/l_o$ | | strength, psi | |
|---|---|---|---|---|---|---|---|---|---|---|---|---|
| | cross | machine | cross | machine | cross | machine | cross | machine | cross | machine | cross | machine |
| SEBS 1/Polymer 1 (80/20) | 69.5 | 142 | 99.6 | 180 | 128 | 230 | 155 | 289 | 14.45 | 14.69 | 1820 | 2160 |
| SEBS 1/Polymer 1 (70/30) | 117 | 170 | 163 | 243 | 219 | 321 | 273 | 398 | 15.61 | 13.41 | 2098 | 2051 |

What is claimed is:

1. A personal hygiene article comprising a soft elastomeric film consisting essentially of a coupled, selectively hydrogenated block copolymer having the general formula:

(A-B)nX wherein
  a. prior to hydrogenation the A block is a polymerized monoalkenyl arene hydrocarbon block having a molecular weight from 6000 to 7000;
  b. prior to hydrogenation the B block is a polymerized conjugated diene hydrocarbon block having a vinyl content from 60 to 85% mol;
  c. the total molecular weight of the block copolymer is from 180,000 to 400,000;
  d. the monoalkenyl arene content of the block copolymer is from 9 to 16% wt;
  e. X is the residue of a coupling agent and n is from 2 to 6; and
  f. the block copolymer includes less than 10% of uncoupled A-B arms;
  where the elastomeric film has a 100% stress of about 100 psi or less and a tensile strength of at least about 1000 psi.

2. The personal hygiene article of claim 1 wherein the total molecular weight of the block copolymer is from 200,000 to 300,000.

3. The personal hygiene article of claim 1 wherein the monoalkenyl arene content is from 10 to 14% wt.

4. The personal hygiene article of claim 1 wherein the monoalkenyl arene is styrene and the conjugated diene is butadiene.

5. The personal hygiene article of claim 4 wherein subsequent to hydrogenation greater than 95% mol of the conjugated diene units and less than 5% mol of the monoalkenyl arene units have been hydrogenated.

6. The personal hygiene article of claim 1 having a tensile elongation of at least 600%.

7. The personally hygiene article of claim 1 which is a glove, diaper, incontinence product, disposable swimwear or disposable undergarment.

8. A soft elastomeric film comprising two coupled, selectively hydrogenated block copolymers each having the general formula:

(A-B)nX wherein the film comprises from 15 to 40 parts by weight of a first block copolymer having:
  a. prior to hydrogenation the A block is a polymerized monoalkenyl arene hydrocarbon block having a molecular weight from 6000 to 7000;
  b. prior to hydrogenation the B block is a polymerized conjugated diene hydrocarbon block having a vinyl content from 60 to 85% mol;
  c. the total molecular weight of the block copolymer is from 180,000 to 400,000;
  d. the monoalkenyl arene content of the block copolymer is from 9 to 16% wt;
  e. X is the residue of a coupling agent and n is from 2 to 6; and
  f. the block copolymer includes less than 10% of uncoupled A-B arms; and the film comprises from 60 to 85 parts by weight of a second block copolymer having:
  g. prior to hydrogenation the A block is a polymerized monoalkenyl arene hydrocarbon block having a molecular weight from 5000 to 7000;
  h. prior to hydrogenation the B block is a polymerized conjugated diene hydrocarbon block having a vinyl content from 60 to 85% mol;

i. the total molecular weight of the block copolymer is from 100,000 to 160,000;
j. the monoalkenyl arene content of the block copolymer is from 16% wt to 24% wt;
k. X is the residue of a coupling agent and n is from 2 to 6; and
l. the block copolymer includes less than 10% of uncoupled A-B arms; and where the elastomeric film has a 100% stress of about 100 psi or less and a tensile strength of at least about 1000 psi.

9. The soft elastomeric film of claim 8 wherein the second block copolymer has a melt index of greater than or equal to 12 g/10 min according to ASTM D1238 at 230° C. and 2.16 kg weight.

10. A glove, diaper, incontinence product, disposable swimwear or disposable undergarment comprising the soft elastomeric film of claim 8.

11. A soft elastomeric film comprising from 25 to 75 parts by weight of a coupled, selectively hydrogenated block copolymer having the general formula:

(A-B)$_n$X wherein
a. prior to hydrogenation the A block is a polymerized monoalkenyl arene hydrocarbon block having a molecular weight from 6000 to 7000;
b. prior to hydrogenation the B block is a polymerized conjugated diene hydrocarbon block having a vinyl content from 60 to 85% mol;
c. the total molecular weight of the block copolymer is from 180,000 to 400,000;
d. the monoalkenyl arene content of the block copolymer is from 9 to 16% wt;
e. X is the residue of a coupling agent and n is from 2 to 6; and
f. the block copolymer includes less than 10% of uncoupled A-B arms and from 75 to 25 parts by weight of a controlled distribution block copolymer having a general configuration A'-B', A'-B'-A', (A'-B')$_n$, (A'-B'-A')$_n$X, (A'-B')$_n$X or mixtures thereof, where n is an integer from 2 to about 30, and X is coupling agent residue wherein:

g. prior to hydrogenation each A' block is a monoalkenyl arene polymer block and each B' block is a controlled distribution copolymer block of at least one conjugated diene and at least one monoalkenyl arene;
h. subsequent to hydrogenation about 0-10% of the arene double bonds have been reduced, and at least about 90% of the conjugated diene double bonds have been reduced;
i. each A' block has a number average molecular weight between about 3,000 and about 60,000 and each B' block has a number average molecular weight between about 30,000 and about 300,000;
j. each B' block comprises terminal regions adjacent to the A' block that are rich in conjugated diene units and one or more regions not adjacent to the A' blocks that are rich in mono alkenyl arene units;
k. the total amount of monoalkenyl arene in the hydrogenated block copolymer is about 20 percent weight to about 80 percent weight;
l. the weight percent of mono alkenyl arene in each B' block is between about 10 percent and about 75 percent; and
m. the monoalkenyl arene blockiness in the B' block is less than 40%;

where the elastomeric film has a 100% stress of about 100 psi or less and a tensile strength of at least about 1000 psi.

12. A glove, diaper, incontinence product, disposable swimwear or disposable undergarment comprising the soft elastomeric film of claim 11.

* * * * *